(12) United States Patent
Singh et al.

(10) Patent No.: US 10,902,745 B2
(45) Date of Patent: Jan. 26, 2021

(54) NEURO-ENDOSCOPE BOX TRAINER

(71) Applicants: Indian Council of Medical Research, New Delhi (IN); All India Institute of Medical Sciences, New Delhi (IN); Indian Institute of Technology, New Delhi (IN); Department of Science & Technology, New Delhi (IN)

(72) Inventors: Ramandeep Singh, New Delhi (IN); Britty Baby, New Delhi (IN); Vinkle Kumar Srivastav, New Delhi (IN); Ashish Suri, New Delhi (IN); Subhashis Banerjee, New Delhi (IN); Prem K. Kalra, New Delhi (IN); Sanjiva Prasad, New Delhi (IN); Subodh Kumar, New Delhi (IN); Kolin Paul, New Delhi (IN); Sneh Anand, New Delhi (IN)

(73) Assignees: All India Institute of Medical Sciences, New Delhi (IN); Indian Institute of Technology, New Delhi (IN)

( * ) Notice: Subject to any disclaimer, the term of this patent is extended or adjusted under 35 U.S.C. 154(b) by 223 days.

(21) Appl. No.: 15/517,801

(22) PCT Filed: Oct. 8, 2015

(86) PCT No.: PCT/IN2015/000381
§ 371 (c)(1),
(2) Date: Apr. 7, 2017

(87) PCT Pub. No.: WO2016/056025
PCT Pub. Date: Apr. 14, 2016

(65) Prior Publication Data
US 2017/0316720 A1    Nov. 2, 2017

(30) Foreign Application Priority Data

Oct. 8, 2014   (IN) .......................... 2875/DEL/2014

(51) Int. Cl.
*G09B 23/28*       (2006.01)
*A61B 90/00*       (2016.01)
(Continued)

(52) U.S. Cl.
CPC ............ *G09B 23/285* (2013.01); *A61B 1/313* (2013.01); *A61B 90/361* (2016.02); *A61B 1/04* (2013.01); *A61B 2017/00707* (2013.01)

(58) Field of Classification Search
CPC ...... G09B 23/285; G09B 23/30; A61B 34/70; A61B 1/313; A61B 2017/00707
See application file for complete search history.

(56) References Cited

U.S. PATENT DOCUMENTS 5,403,191 A    4/1995  Tuason
5,620,326 A *  4/1997  Younker ................ G09B 23/28
                                                      434/268
(Continued)

FOREIGN PATENT DOCUMENTS

CN    1226707 C    11/2005
CN    2751372 Y    1/2016
(Continued)

*Primary Examiner* — Melba Bumgarner
*Assistant Examiner* — Amir A Klayman
(74) *Attorney, Agent, or Firm* — Woodard, Emhardt, Henry, Reeves & Wagner, LLP

(57) ABSTRACT

An electro-mechanical box trainer for neurosurgery comprise: (i) a base part which comprises a rubberized working port (11) for insertion of endoscope (26) and tool (25) for manipulation, a microcontroller programmed motorized peg plate (14) placed at 45° degrees of inclination for defining a practice volume according to the neuroendoscopy, a membrane keypad to change the angle of rotation of said peg (Continued)

plate (14) along vertical axis, liquid crystal display (LED) array to illuminate the interior of the box and a removable base plate (6) to house the circuitry; and (ii) a removable part enclosed of five walls such as a front wall (18), two lateral walls (17 and 19), a back wall (20) and a top wall (23), comprises a housing to mount an auxiliary camera (32) to record all the task for evaluation and a slider at the back to adjust the camera focus.

6 Claims, 5 Drawing Sheets

(51) Int. Cl.
*A61B 1/313* (2006.01)
*A61B 1/04* (2006.01)
*A61B 17/00* (2006.01)

(56) References Cited

U.S. PATENT DOCUMENTS

| | | | | |
|---|---|---|---|---|
| 5,722,836 A * | 3/1998 | Younker | ............... | G09B 23/285 434/258 |
| 5,947,743 A * | 9/1999 | Hasson | ................ | G09B 23/286 434/262 |
| 6,488,507 B1 | 12/2002 | Stoloff et al. | | |
| 6,517,354 B1 | 2/2003 | Levy | | |
| 6,659,776 B1 * | 12/2003 | Aumann | ............... | G09B 23/285 434/262 |
| 6,790,043 B2 | 9/2004 | Aboud | | |
| 6,887,082 B2 * | 5/2005 | Shun | ..................... | G09B 23/28 434/267 |
| 7,404,716 B2 * | 7/2008 | Gregorio | ............. | G09B 23/285 434/262 |
| 7,821,496 B2 * | 10/2010 | Rosenberg | ........... | G09B 23/285 345/161 |
| 7,850,456 B2 | 12/2010 | Chosack et al. | | |
| 7,866,983 B2 | 1/2011 | Hemphill | | |
| 7,931,470 B2 | 4/2011 | Alexander et al. | | |
| 7,931,471 B2 | 4/2011 | Senagore et al. | | |
| 8,007,281 B2 * | 8/2011 | Toly | ....................... | A61B 90/36 434/262 |
| 8,007,282 B2 * | 8/2011 | Gregorio | ................ | A61B 34/70 434/272 |
| 8,105,089 B2 | 1/2012 | Hudson | | |
| 8,469,716 B2 * | 6/2013 | Fedotov | ................ | G09B 23/285 434/262 |
| 8,764,452 B2 | 7/2014 | Pravong et al. | | |
| 9,418,574 B2 * | 8/2016 | Park | ........................ | G09B 23/32 |
| 9,579,088 B2 * | 2/2017 | Farritor | ............ | A61B 17/00234 |
| 9,959,785 B2 * | 5/2018 | Tortola | .................. | G09B 23/285 |
| 10,108,266 B2 * | 10/2018 | Banerjee | ............. | G06F 3/03545 |
| 10,121,391 B2 * | 11/2018 | Breslin | ................... | G09B 23/30 |
| 10,682,126 B2 * | 6/2020 | Sial | ........................ | A61B 34/20 |
| 2004/0024418 A1 * | 2/2004 | Irion | ....................... | G09B 19/24 606/205 |
| 2005/0142525 A1 * | 6/2005 | Cotin | ...................... | G16H 20/40 434/262 |
| 2007/0166682 A1 * | 7/2007 | Yarin | .................... | G09B 23/285 434/267 |
| 2007/0238081 A1 * | 10/2007 | Koh | ...................... | G09B 23/285 434/262 |
| 2013/0327836 A1 * | 12/2013 | Prpa | ........................ | A61B 90/98 235/470 |
| 2014/0051049 A1 * | 2/2014 | Jarc | ......................... | G09B 23/30 434/267 |
| 2014/0087348 A1 * | 3/2014 | Tracy | .................... | G09B 23/285 434/272 |
| 2014/0220527 A1 * | 8/2014 | Li | ............................ | G09B 9/00 434/262 |
| 2014/0349265 A1 * | 11/2014 | Park | ........................ | G09B 23/32 434/272 |
| 2015/0037773 A1 * | 2/2015 | Quirarte Catano | .. | G09B 23/285 434/262 |
| 2016/0133158 A1 * | 5/2016 | Sui | ........................ | G09B 23/285 434/262 |
| 2016/0140876 A1 * | 5/2016 | Jabbour | .................. | G09B 23/285 434/262 |
| 2016/0247418 A1 * | 8/2016 | Folzenlogen | ........ | G09B 23/285 |
| 2018/0286287 A1 * | 10/2018 | Razzaque | ............ | G09B 23/286 |
| 2019/0172370 A1 * | 6/2019 | Ormond | ................ | G09B 23/30 |

FOREIGN PATENT DOCUMENTS

| | | |
|---|---|---|
| CN | 102208151 B | 9/2016 |
| WO | WO 2008/041021 A1 | 4/2008 |
| WO | WO 2013/028847 A1 | 2/2013 |

* cited by examiner

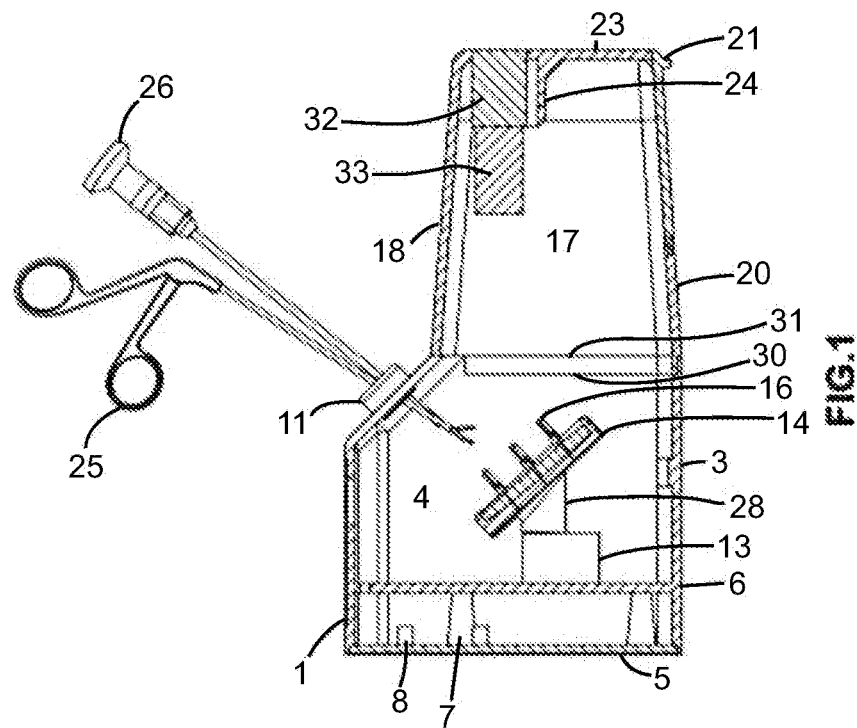
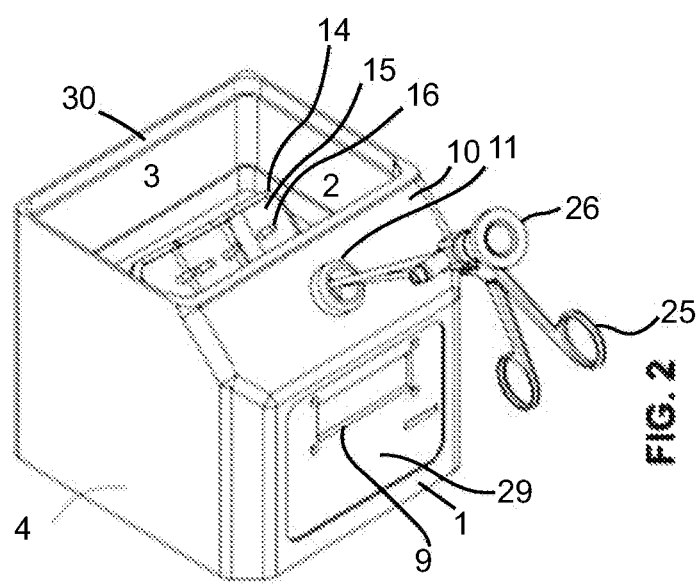
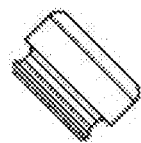
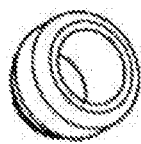
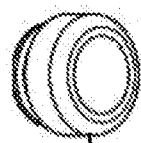
FIG. 3

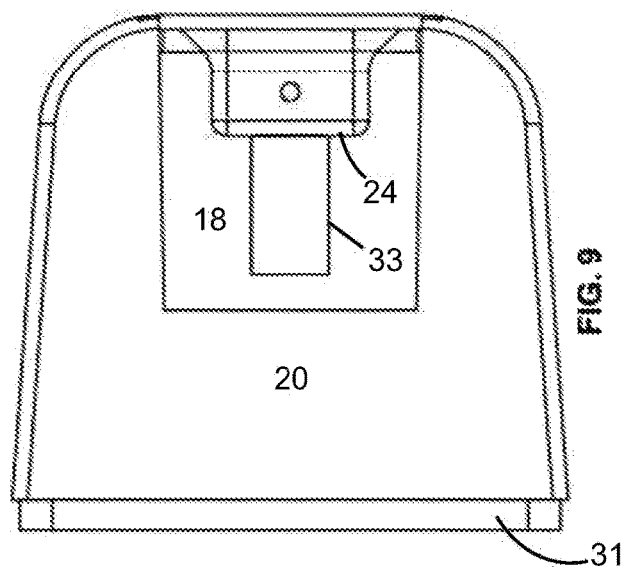
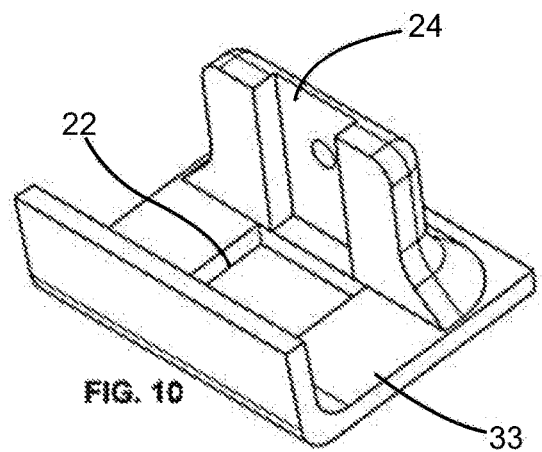

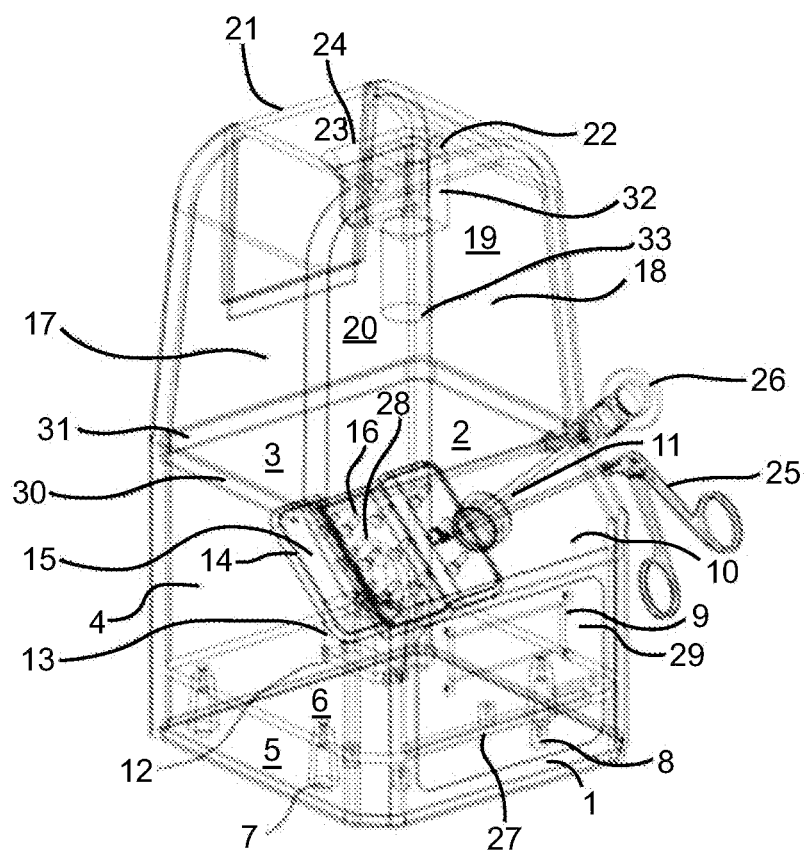
Figure : 11

NEURO-ENDOSCOPE BOX TRAINER

CROSS-REFERENCE TO RELATED APPLICATIONS

This application is a National Stage of International Application No. PCT/IN2015/000381, filed Oct. 8, 2015, which claims the benefit of Indian Patent Application No. 2875/DEL/2014, filed Oct. 8, 2014, each of which is hereby incorporated by reference in their entirety.

FIELD OF INVENTION

The present invention relates to minimally invasive neurosurgery training apparatus, and more particularly to a neuro-endoscopic box trainer to improve eye-hand coordination, dexterity, efficiency of motion, instrument-tissue manipulation and endoscope manipulation. The present invention further provides a neuro-endoscope box trainer that also includes an auxiliary camera for recording and offline analysis of the performed activity of the user.

BACKGROUND AND PRIOR ART OF THE INVENTION

Neurosurgical procedures are highly complex and the margin for error is very less. Even a minor error made by the surgeon can lead to serious consequences like paralysis and even death. Neurosurgical techniques are shifting towards minimally invasive procedures. Technological advancements in minimally invasive techniques challenge the neurosurgeons to improve their skills.

Neuro-endoscopy is a minimally invasive procedure where the endoscope is used to access the deep structures of the brain. The endoscopic camera is used to navigate through the brain and image is displayed on a monitor. Depth information can be interpreted by the motion of the endoscopic camera. The learning process of such surgical procedures takes long time and apprenticeship model based learning is not adequate. Iatrogenic errors have drawn increasing attention to the dexterity of surgeons that require elaborate and effectual training.

Due to the constraints of extremely fine movements and size of the eloquent structures involved in neurosurgery, skills training and evaluation tools are not highly developed. Training can be imparted either on evaluation systems like box trainers or on virtual training platforms. Due to multi-disciplinary technological hurdles, the virtual simulators do not provide the level of realism similar to the operating environment expected by the surgeon. Rather honing of the surgical skills by performing simple tasks on trainers would help the surgeons to improve each component in a targeted way. Preliminary eye hand coordination training of these minimally invasive surgical skills on cadavers and animals is not feasible due to their short supply. Cadavers and animals based training should be practiced only after attaining a certain level of psychomotor skills on box trainers.

CN 102208151 A discloses an operation training box of neuroendoscopy that relates to an operation training box of a neuroendoscopy, and the operation training box comprises a box top, a box body and a box bottom, at least one operation training hole is arranged on the box top, an operation training pipe is arranged below the operation training hole; a head end of the operation training pipe is fixedly connected with an inner wall of the operation training hole, a tail end of the operation training tube is suspended above the box bottom; a groove is formed above the box bottom and under the operation training pipe; a vertical box body position fixing plate is arranged on the edge of the box bottom; the neuroendoscopy and associated surgical equipment are arranged in the box through the operation training pipe; and a trainer can perform the operation training through a surgical equipment handle out of the operation box. The operation training box of the neuroendoscopy is similar with the environment and important condition of the neuroendoscopy operation, and is simple in structure, low in manufacturing cost, convenient for training, easy for repeated operation and popularization; the operation training box of the neuroendoscopy can be used for performing the skill training to the professional, and is convenient to use.

CN App No. 101589416B provided an endotrainer that relates to a device for medical practitioners to practice techniques used in endoscopic surgery. A portable, folding-laptop style endotrainer, the endotrainer comprising: a base defining a work area for endotraining; a camera for viewing the work area; one or both of i) a display screen for displaying an image from the camera the display screen being attached to the base; and ii) a wireless or wired link coupled to the camera for connecting the camera to a display screen; and a fold-up endotraining dashboard, the endotraining dashboard having at least one portal to enable access of a surgical instrument to the work area; and wherein the endotrainer has two configurations, a first, folded configuration in which the endotrainer is folded substantially flat and a second, operational configuration in which the display screen, if present, is unfolded to a viewing position for an operator of the endotrainer and in which the endotraining dashboard is unfolded such that it is displaced away from the base for endotraining.

WO App. No. 2013028847A1 disclosed an application and method for surgical skills training that relates to a surgical skills training system comprises: a trainer platform assembly including a training platform; a base, the base configured to accommodate at least one target array; the target array including a planar surface upon which are disposed a plurality of protruding targets oriented at a plurality of angles on the base; a left side support for supporting the training platform on the base; and a right side support for supporting the training platform on the base.

U.S. Pat. No. 6,488,507 B1 provided a portable surgical trainer that discloses a portable enclosure for simulating surgical conditions using endoscopic instruments. The enclosure contains a pump and fluid reservoir and a canister in which an animal or synthetic tissue sample is placed within an adjustable cavity. The pump circulates fluid to an endoscopic instrument external to the enclosure enabling an individual to practice either monopolar or bipolar instrument techniques within the cavity and under conditions that simulate real life operating conditions.

U.S. Pat. No. 7,837,473B2 disclosed a surgical training device and method that relates to a surgical training device and method. The surgical training device can include a portable case including a base and a lid. The surgical training device can include a support coupled to the base, and the support can be moveable from a first position stored within the base to a second position coupled to the lid. The support can include a plurality of ports positioned so that when the support is in the second position, the surgical instruments inserted into the plurality of ports are substantially horizontal and parallel to the base. The surgical training device can include a camera and a video monitor connected to the camera. The video monitor can display an output from the camera including the surgical instruments and/or simulated tissue.

U.S. Pat. No. 6,790,043 B2 provided a method and apparatus for surgical training that highlights an apparatus and method for microsurgical training using cadaveric anatomy with filling of the vascular system by fluids under pressure to simulate the appearance and function of live surgery. One or more arteries on the specimen of cadaveric anatomy are cannulated and connected to an arterial reservoir having a flexible container holding an arterial fluid simulating the appearance of blood circulating in the arteries of the living organism from which the cadaveric anatomy is derived. Suitable static pressure simulating the arterial pressure appropriate to that of the living organism is applied to the air in an air-tight space surrounding the flexible container in the arterial reservoir. A pulsating machine provides air pulsations to the space surrounding the flexible fluid container to simulate the normal pulsations of the arterial system. One or more veins on the specimen are also cannulated and connected to a venous reservoir having a flexible container holding a venous fluid simulating the appearance of blood circulating in the veins of the living organism. Suitable static pressure simulating the venous pressure appropriate to that of the living organism is applied to the air in an air-tight space surrounding the flexible container in the venous reservoir. Optionally, if the specimen includes at least a portion of spinal canal, a clear fluid reservoir can be connected to the specimen through the spinal canal to simulate cerebrospinal fluid.

U.S. Pat. No. 6,517,354B1 disclosed a medical simulation apparatus and related method that discloses a medical simulation apparatus may include a housing, a vessel simulating tube carried by the housing, a liquid reservoir carried by the housing, a pump carried by the housing for circulating the liquid from the liquid reservoir through the vessel simulating tube, and an access port in fluid connection with the vessel simulating tube for receiving an instrument therein. The pump may be a pulsatile pump for providing a pulsed liquid circulation simulating blood flow. Also, the vessel simulating tube may include an elastic material (e.g., silicone) expandable with the pulsed liquid circulation. Furthermore, the vessel simulating tube may include a portion having an enlarged diameter simulating an aneurysm, or it may include a portion having a restriction simulating a stenosis. Alternately, the vessel simulating tube may include a portion simulating an arteriovenous malformation or tumor.

U.S. Pat. No. 7,850,456 B2 provided a surgical simulation device, system and method that relates to a device system and method for simulating laparoscopic procedures, particularly for the purposes of instruction and/or demonstration. The system comprises one or more virtual organs to be operated on. The organ comprises a plurality of elements, each element having neighboring elements; and a plurality of tensioned connections connecting neighboring elements over said organ, such that force applied at one of said elements propagates via respective neighboring elements provides a distributed reaction over said organ. In addition there is a physical manipulation device for manipulation by a user; and a tracking arrangement for tracking said physical manipulation device and translating motion of said physical manipulation device into application of forces onto said virtual organ. The system is capable of simulating organs moving, cutting, suturing, coagulations and other surgical and surgery-related operations.

U.S. Pat. No. 8,764,452 B2 disclosed a portable laparoscopic trainer that explains a portable surgical training device. The trainer includes a top cover spaced apart from a base to form a simulated body cavity for locating model organs that are substantially obscured from the field of view of the user. The top cover includes a video display, fixed insertion ports and interchangeable inserts containing simulated tissue layers. The training device has open sides for demonstrating and training lateral surgical techniques including a simulated or live tissue colon attached to a support leg for simulating transanal minimally invasive surgery. A training endoscope with an adjustable focal length for use with the trainer and, in particular, with optical trocars is disclosed. The surgical trainer can be angled and is well suited for training laparoscopic surgery techniques and demonstrating surgical instruments.

U.S. Pat. No. 7,866,983B2 disclosed a surgical simulator system that relates a surgical simulator for teaching, practicing, and evaluating surgical techniques. Such a simulator may comprise a cassette of organs, blood vessels, and tissues that may be disposable. The simulator also comprises a hemodynamic simulator and a frame assembly, the frame assembly providing support for the cassette of organs as well as a fluid conduit through which simulated blood flow from the hemodynamic simulator may be connected to the blood vessels of the organs and related tissues. The hemodynamic simulator provides adjustable and variable pressures to the arteries and veins, as well as variable pulse rates, which can be programmed at settings chosen by an instructor or user.

U.S. Pat. No. 7,931,470B2 relates to an interface device and method for interfacing instruments to medical procedure simulation systems which explains an interface device and method for interfacing instruments to a medical procedure simulation system serve to interface peripherals in the form of mock medical instruments to the medical procedure simulation system computer to enable simulation of medical procedures. The interface device includes a housing having a mock bodily region of interest to facilitate insertion of a mock instrument, such as an endoscope tube, into the interface device. The mock bodily region of interest may be pivotable to simulate various patient orientations. The instrument is engaged by a capture mechanism in order to measure rotational and translational motion of the instrument. An actuator is disposed within the interface device to provide force feedback to the instrument. The measured motion is provided to the computer system to reflect instrument motion on the display during the simulation. Alternatively, the interface device may be configured to accommodate instrument assemblies having a plurality of nested instruments (e.g., sheath, catheter and wire), whereby the interface device individually grasps, and measures manipulation of and provides force feedback to the nested instruments. In addition, the interface device may be configured to simultaneously accommodate a plurality of independently inserted instruments.

U.S. Pat. No. 7,931,471B2 disclosed a surgical training aid apparatus that relates to a surgical training aid apparatus for facilitating the training of medical procedures comprising a housing and an anatomical replicating assembly. The housing includes a tray having a bottom surface and a top surface opposite the bottom surface. The anatomical replicating assembly is positioned upon the top surface of the tray of the housing, and includes a base layer and at least one body component. The base layer has a bottom surface and a top surface, and, overlays a portion of the top surface of the tray of the housing. The base layer further includes a tackiness. The body component is positioned between the top surface of the housing and the bottom surface of the base layer or on the base layer. The body component likewise includes a tackiness. The body component is releasably coupled to the base layer due to the tackiness of the two components, wherein the tackiness is overcome so as to separate the at least one body component relative to the base layer.

U.S. Pat. No. 8,105,089 B2 relating to a medical procedures training model highlights a training model for use in training to perform a medical procedure which is invasive of a skull, such as the insertion of an external ventricular drain or the evacuation of a subdural hematoma. The training model may comprise a base component defining a training component receptacle and a training component for mounting in the training component receptacle and comprising a skull section. Alternately, the training model may comprise the skull section or the training component in isolation. The skull section comprises an outer skull layer, a middle skull layer and an inner skull layer. The outer skull layer is constructed of an outer skull material which simulates osseous tissue when penetrated. The middle skull layer is constructed of a middle skull material which simulates marrow tissue when penetrated. The inner skull layer is constructed of an inner skull material which simulates osseous tissue when penetrated.

CN App. No 1226707 C disclosing a method and system for simulation of surgical procedures explains that it is provided by the computer unit is used in a virtual environment, the target in the body, such as the organs during surgery simulation method and system. The goal of the virtual environment, including the physical description of the three-dimensional mathematical model, which reflects the physical and mechanical properties of the target geometry, as well as virtual instruments, controlled by the physical feeding device, which makes it possible to affect the model. The method comprising the steps of: a video sequence that the two-dimensional projection of the model, the real body of the video sequence includes the target record view and interact only with the model engagement virtual instrument. Further, the present invention also relates to the process simulation contains several surgical surgical methods.

CN App. No 2751372 Y provides a laparoscope simulated training table that relates to a laparoscope simulated training table which comprises an abdomen mold box, a camera and a monitor. The utility model is characterized in that the abdomen mold box simulates an artificial pneumoperitoneum condition in a laparoscopic operation; the camera is arranged in the abdomen mold box and is connected with the monitor out of the box through a conducting wire; the surface of the abdomen mold box is provided with joining holes in which laparoscope operation instruments are arranged; simulated human organism fittings are arranged in the abdomen mold box. The laparoscope simulated training table of the utility model can help trainees to train the technical actions of separation, tongs clamping, hemorrhage stop, anastomosis, suture, ligation, etc. in a laparoscopic operation. The utility model is free from the limitation of time and space, so that trainees can rapidly have an acquaintance with and master the basic operation of laparoscopic operation. The utility model has the advantages of simple structure and convenient operation.

U.S. Pat. No. 5,403,191 A disclosed a laparoscopic surgery simulator and method of use that relates to an apparatus used in simulating the human body cavity whereby an individual user can practice endoscopic surgical procedures by duplicating the operative steps performed on actual true to life condition for the purpose of learning the art and constantly improving the skill of eye-hand coordination and manual dexterity. The simulator is provided with open sides to gain access into the cavity for placement of objects simulating human organs which are then mounted and anchored inside the cavity for practice simulation in instrument manipulation. Surgical instruments are inserted into the cavity through the pre-established apertures on the transparent plastic panel and the instruments are manipulated while performing the practice procedure without the benefit of direct binocular vision on the object-simulations; instead the trainee imitates and directs the activities inside the cavity under vision using the endoscopic-video-monitor system or by similar indirect viewing method provided by the reflecting mirrors of the two mirror concept, thus mimicking a real life operative condition.

US App. No. 20040033476 A1 provides a laparoscopic trainer that highlights a surgical training device for the practice of surgical techniques. The device comprises an operation area arranged to receive an operable structure and a screening wall having an aperture. The wall is positioned relative to the operation area such that the wall prevents direct viewing of the operation area from at least one position external the wall. The device further includes an optical system comprising a first mirror and a second mirror. The first mirror is arranged to reflect a primary image of the operation area to the second mirror which in turn is arranged to reflect a secondary image of the operation area that is visible from the external position. The position and orientation of the mirrors and the aperture is such that only the secondary image of the operation area is visible from the external position.

However, the prior arts do not disclose trainers for Neuro-endoscopy training and most of the prior art discloses laparoscopic stimulators and trainers. The present invention discloses a novel box trainer that has been designed, to provide an enclosed constrained environment required for endoscopic neurosurgical training. The neuro-endo box trainer comprises of peg plate that is placed at 45 degrees to provide inclination parallel to the endoscope insertion wall. Further the peg plate have a trough of 10 mm to provide variable depths for manipulation in all three axes. Further, the motorized movement of peg plate along Z-axis to increase the difficulty of task and to acquaint the trainee with variable angle scopes.

Further, the neuro-endoscope box trainer as disclosed by the present invention comprise of an auxiliary camera to record the activity of performed task and to analyze parameters such as hitting the plate, dropping the rings, motion smoothness of the instrument and scope.

OBJECTS OF THE INVENTION

It is therefore, an object of the present invention is to provide a cost effective box trainer for minimally invasive neuro-endoscopy.

It is another object of the present invention is to provide a constrained environment similar to neurosurgical workspace, and evaluate their skills using auxiliary camera.

Yet another object of the present invention is to provide different levels of difficulty to perform basic tasks like pick and place while manipulating objects having tissue-like properties with the help of an endoscopic display.

SUMMARY OF THE INVENTION

According to this present invention, there is provided an electro-mechanical box trainer for neurosurgery comprises: (i) a base part which comprises a rubberized working port

(11) for insertion of endoscope (26) and tool (25) for manipulation, a microcontroller programmed motorized peg plate (14) placed at 45° degrees of inclination for defining a practice volume according to the neuro-endoscopy, a membrane keypad to change the angle of rotation of said peg plate (14) along vertical axis, liquid crystal display (LED) array to illuminate the interior of the box and a removable base plate (6) to house the circuitry; and (ii) a removable part enclosed of five walls such as a front wall (18), two lateral walls (17 and 19), a back wall (20) and a top wall (23), comprises a housing to mount an auxiliary camera (32) to record all the task for evaluation and a slider at the back to adjust the camera focus;

said the working port (11) leads to an activity area to perform pick and place task by manipulating rubber rings placed on the peg;

said motorized peg plate (14) has a manipulation area of 60×40 mm, a through of 10 mm in the middle for providing variable depth of manipulation;

four column and three rows of 4 mm diameter and 15 mm height, among which the lateral columns are on flat region and middle columns are on the through region;

the rubberized surface, rubber rings to perform the activity of pick and place, twelve pegs which are made up of ABS plastic;

said removable base plate is fixed to the bottom wall (5) of the base part comprises screw fixator (7) and circuit board fixator (8);

the removable base plate is fixed to the servomotor (13) with slote providing space for electronic components;

said auxiliary camera is mounted to the stand focuses the interior peg plate (14) and records the activity of the user using a wide angle less and hence suitable for capturing endoscope and instrument motion effectively;

said membrane keypad determines the angle of the peg plate which can be changed from −45° to +45° to decrease the difficulty of the task;

the LED array placed on the above one-third portion of base port too illuminate the interior of the trainer;

BRIEF DESCRIPTION OF THE ACCOMPANYING DRAWINGS

FIG. 1 is a section view of the Neuro-Endo-Trainer along with the instrument and endoscope in their functional positions entering the base part through the pre-established aperture on the box;

FIG. 2 is the isometric view of base part.

FIG. 3 is the isometric view of the rubberized working port.

FIG. 9 is the back view of removable top part.

FIG. 10 is the isometric view of the camera mount

FIG. 11 is the Neuro-Endo Box Trainer.

DETAILED DESCRIPTION OF THE INVENTION

Figure 4:
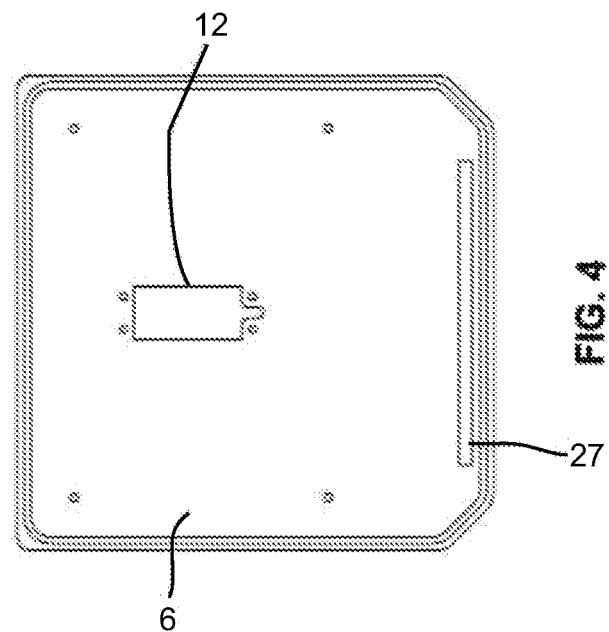
FIG. 4 is the top view of base part.

According to this present invention, there is provided a box trainer for neuro-endoscopy that comprises of a base part and a removable top part. The base consists of a rubberized opening in the front for insertion of endoscope and tool for manipulation, a microcontroller programmed motorized peg plate defining a practice volume according to the neuro-endoscopy working environment for pick and place task, rubber sheet to cover the peg plate and rubber rings for manipulation, a membrane keypad to change the angle of rotation of peg plate along vertical axis, a liquid crystal display in the front to show corresponding angle of peg plate, a stand to mount the servo motor to the bottom of the base part, a removable base plate to house the circuitry and other components, light emitting diode array to illuminate the interior of the box. The top of the box consists a housing to mount the auxiliary camera to record the task for evaluation and a slider at the back to adjust the camera focus.

FIG. 1 depicted an electro-mechanical box trainer for neurosurgery education and training, particularly for neuro-endoscopic endo-nasal surgical training. The base part formed from opaque ABS plastic material comprises of 5 walls to provide enclosed area.

The base part depicted in FIG. 2 includes a rubberized working port 11 on the face wall 1 in which the upper one third portion is inclined at 45 degrees 10 and is having a 20 mm aperture as in FIG. 3 with a rubber port in the middle 11 for insertion of endoscope 26 and tool 25. The lateral walls are 2 and 4 and the back wall is 3. The bottom wall is 5 on to which the removable base plate is fixed. Lower two third portion of front wall 1 has slot 9 to fix the liquid crystal display and slot 29 for membrane keypad. The membrane keypad determines the angle of the peg plate, which can be changed from −45 degree to +45 degree to increase the difficulty of the task.

Inside of base part contains a removable base-plate 6 as in FIG. 4 with a slot 12 to fix the servomotor 13 and has a slot 27 to provide space for electronic components.

Figure 5:
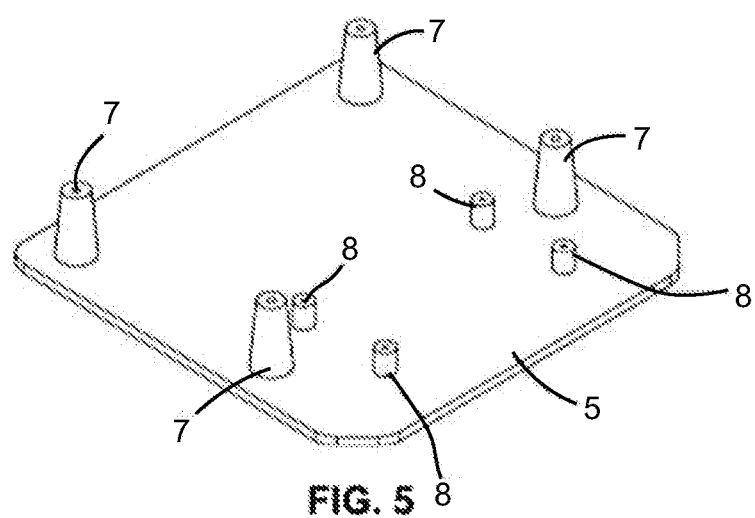
FIG. 5 is the isometric view of the bottom wall of base part.

Removable base plate 6 is fixed to the bottom wall 5 of the base part, which contains screw fixators 7 and circuit board fixators 8 as shown in FIG. 5. discloses a LED array which is placed on the above one-third portion of base part to illuminate the interior of the trainer. A 10 mm groove 30 has been made on the top of the inner wall of the base part for firm fixation of the removable upper part. There is a circular opening at the back wall of the base part to provide power supply to the circuit.

The box trainer for neuro-endoscopic surgical training basically comprising of enclosed working area to block the trainee's direct line of sight of the activity area. Furthermore, the endoscope of brand X and tool of brand Y are inserted through a rubberized working port. The working port leads to an activity area to perform pick and place task by manipulating rubber rings placed on the pegs and there is another rubberized platform placed on the activity area.

In one aspect a method of psychomotor skills training is provided. Embodiment consists of providing variable depth perception activity with the help of uneven and slanted manipulation area. In another aspect the axial rotation of the activity area further increases the difficulty level of depth manipulation. Dimensional constraints of activity area are provided so as to replicate the real surgery scenario of endo-nasal neuro-endoscopic surgery. Angular constraints of axial rotations of activity area are decided so as to acquaint the trainee with the use of different angled endoscopes.

Figure 6:
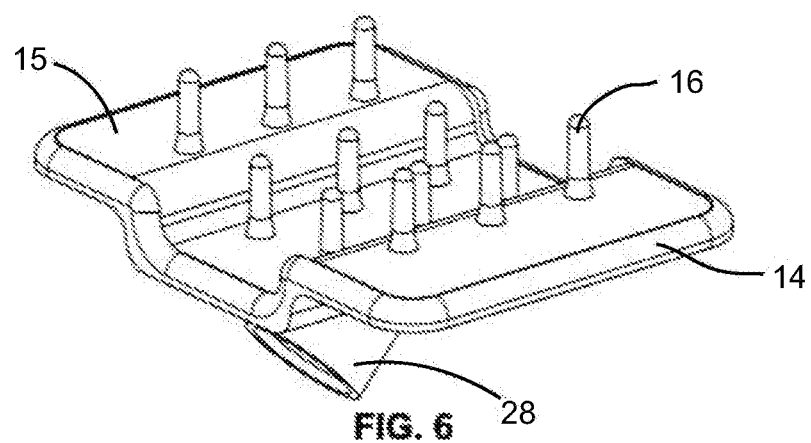
FIG. 6 is the isometric view of the peg plate.

From FIG. 6, it is evident that a motorized peg plate 14 with twelve pegs 16 are made of ABS plastic and plate 14 is mounted over to the servomotor 13 using a stand 28. It has rubberized surface 15 and rubber rings around the pegs to perform the activity of pick and place. Peg plate 14 has a manipulation area of 60×40 mm, a trough of 10 mm in the middle to provide variable depth of manipulation, four columns and three rows of pegs 16 of 4 mm diameter and 15 mm height, among which the lateral columns are on the flat region and middle columns are on the trough region. Height of the pegs has been designed in such a way that it provides a medium level of difficulty during placement of rings of variable diameter (8, 9, 10 mm). On top of peg plate 14, a rubber sheet 15 is placed to provide a sense of tissue.

Figure 7:
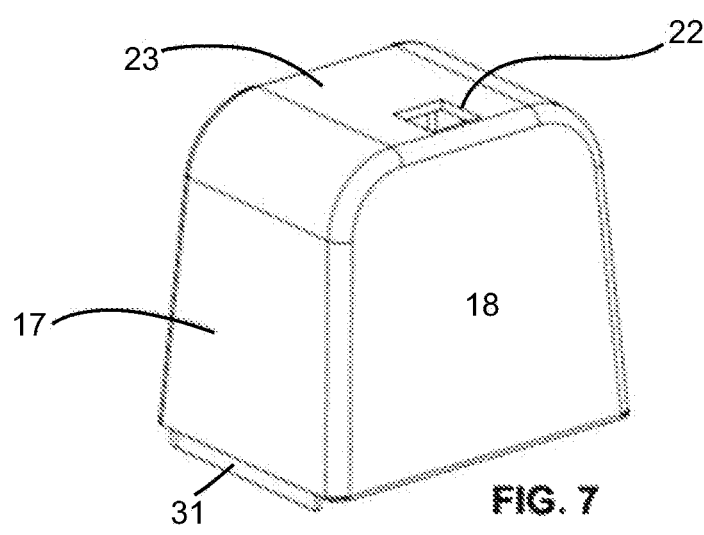
FIG. 7 is the isometric view of the removable top part.
Figure 8:
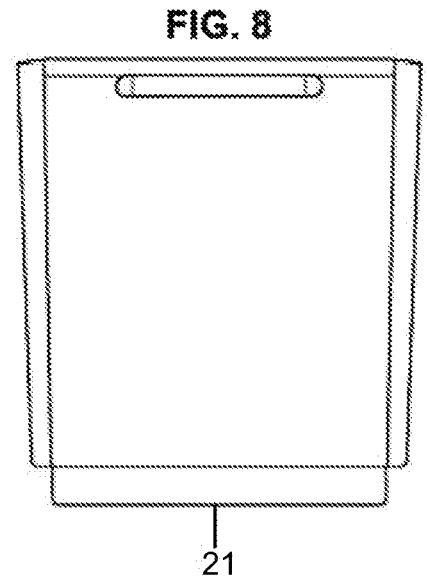
FIG. 8 is the front view of the slider.

FIG. 7 discloses an upper removable part enclosed of 5 walls. It has a front wall 18, two lateral walls 17 and 19, a back wall 20 with a rectangular slider 21 as shown in FIG. 8 for focus adjustment of the camera, a top wall 23 that has a stand 24 towards inside for fixation of the auxiliary camera 32 and a slot 22 for the camera wiring. Lower end of the upper part has an extrusion 31 of 10 mm for its attachment to base part.

FIG. 9 shows auxiliary camera 32 mounted to the stand 24 focuses the interior peg plate 14 and records the activity of the user using a wide-angle lens 33.

FIG. 10 discloses the isometric view of the camera mount. The videos are recorded through Ethernet to the desktop or laptop and saved to the hard disk. The placement of camera is appropriately chosen to capture endoscope and instrument motion effectively. The video recordings are used for offline analysis of the psychomotor skills of trainee.

According to another embodiment of the invention, a camera of brand Z has been placed at the top so as to capture the entire activity inside the box. Thereby, the captured video data can be analyzed offline to score the efficiency of the activity of the trainee. Yet another embodiment of the invention relates to recording the activity using the endoscopic camera of brand X for further analysis of skills.

The trainee performs the activity of pick and place of the ring in a row-wise manner from right object area to the left target area. After finishing the rows, the trainee replaces the rings to the object area in a diagonal manner.

We claim:

1. An electro-mechanical box trainer for neurosurgery comprising:
   (i) a base part comprising:
      a. a rubberized working port (11) defining an aperture of 20 mm for insertion of endo scope (26) and tool (25) for manipulation;
      b. a microcontroller programmed motorized peg plate (14) having a rubberized surface (15) placed at 45° degrees inclination, having a manipulation area of 60 mm×40 mm divided into a flat region and a trough region in the middle, wherein the trough region has a depth of 10 mm, and wherein the peg plate comprises 12 pegs each having a diameter of 4 mm and height of 15 mm positioned into four columns and three rows, and wherein the four columns are placed such that two columns are in the flat region and two columns are in the trough region;
      c. a slot (29) and a membrane keypad to change the angle of rotation of said microcontroller programmed motorized peg plate (14) along vertical axis, wherein the angle of rotation of the peg plate can be changed from −45° to +45°;
      d. liquid crystal display (9) to show the corresponding angle of peg plate (14), and
      e. a removable base plate (6) to house circuitry;
      f. rubber rings; and
   (ii) a removable part enclosed of five walls comprising a front wall (18), two lateral walls (17 and 19), a back wall (20) and a top wall (23), comprises a housing comprising an auxiliary camera (32) to record all the task for evaluation and a slider at the back wall to adjust the camera focus.

2. An electro-mechanical box trainer for neurosurgery as claimed in claim 1, wherein insertion of the endoscope and tool through the working port (11) provides access to an activity area to perform pick and place task by manipulating the rubber rings placed on the peg.

3. The electro-mechanical box trainer as claimed in claim 1, wherein the pegs are made of ABS plastic.

4. The electro-mechanical box trainer as claimed in claim 1, wherein the removable base plate (6) which is fixed to a bottom wall (5) of the base part comprises screw fixator (7) and circuit board fixator (8).

5. The electro-mechanical box trainer as claimed in claim 3, wherein the removable base plate (6) is fixed to a servomotor (13) with slate providing space for electronic components.

6. The electro-mechanical box trainer as claimed in claim 1, wherein the auxiliary camera (32) mounted to a stand focuses the peg plate (14) and records the activity of the user using a wide-angle lens.

* * * * *